United States Patent
Jeon et al.

(10) Patent No.: US 10,137,156 B2
(45) Date of Patent: Nov. 27, 2018

(54) COMPOSITION COMPRISING NEURAL CELL AND ELASTIN-LIKE POLYPEPTIDE FOR TREATING PARKINSON'S DISEASE

(71) Applicant: DAEGU GYEONGBUK INSTITUTE OF SCIENCE AND TECHNOLOGY, Daegu (KR)

(72) Inventors: Won Bae Jeon, Daegu (KR); Jung-Hee Kim, Daegu (KR); Kyeong-Min Lee, Daegu (KR); Seong-Kyoon Choi, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 0 days.

(21) Appl. No.: 14/929,435

(22) Filed: Nov. 2, 2015

(65) Prior Publication Data

US 2016/0228470 A1    Aug. 11, 2016

(30) Foreign Application Priority Data

Nov. 7, 2014 (KR) .................. 10-2014-0154536

(51) Int. Cl.
| | |
|---|---|
| *A61L 27/34* | (2006.01) |
| *A61L 31/10* | (2006.01) |
| *A61K 35/30* | (2015.01) |
| *A61L 27/36* | (2006.01) |
| *A61L 31/16* | (2006.01) |
| *C07K 14/78* | (2006.01) |
| *A61K 9/00* | (2006.01) |
| *A61K 38/39* | (2006.01) |

(52) U.S. Cl.
CPC ............ *A61K 35/30* (2013.01); *A61K 9/0019* (2013.01); *A61K 38/39* (2013.01); *A61L 27/34* (2013.01); *A61L 27/3675* (2013.01); *A61L 31/10* (2013.01); *A61L 31/16* (2013.01); *C07K 14/78* (2013.01)

(58) Field of Classification Search
CPC combination set(s) only.
See application file for complete search history.

(56) References Cited

FOREIGN PATENT DOCUMENTS

| KR | 20010099203 A | 11/2001 |
|---|---|---|
| KR | 101350900 B1 | 1/2014 |
| KR | 20140030396 A | 3/2014 |

OTHER PUBLICATIONS

Wang et al., Biomaterials, 74:89-98, Sep. 30, 2015.*
Ben-Hur et al., Stem Cells, 22:1246-1255, 2004.*
Betre et al., Biomacromolecules, 3(5):910-916, 2002.*
Jeon et al: "Stimulation of fibroblasts and neuroblasts on a biomimetic extracellular matrix consisting of tandem repeats of the elastic VGVPG domain and RGD motif", Journal of Biomedical Materials Research A, vol. 97, pp. 152-157, 2011.

* cited by examiner

*Primary Examiner* — Kimberly Ballard
*Assistant Examiner* — Stacey N MacFarlane
(74) *Attorney, Agent, or Firm* — Gokalp Bayramoglu

(57) ABSTRACT

The present invention relates to a composition including neural cells and an elastin-like polypeptide for treating Parkinson's diseases. More particularly, the present invention relates to a composition for treating Parkinson's diseases, which can more effectively increase a survival rate and settling rate of neural cells transplanted to an acutely or chronically damaged nerve region for treatment of Parkinson's disease, by simultaneously administering an elastin-like polypeptide with neural cells.

4 Claims, 7 Drawing Sheets

Specification includes a Sequence Listing.

COMPOSITION COMPRISING NEURAL CELL AND ELASTIN-LIKE POLYPEPTIDE FOR TREATING PARKINSON'S DISEASE

CROSS-REFERENCE TO RELATED APPLICATIONS

This U.S. non-provisional patent application claims priority under 35 U.S.C. § 119 of Korean Patent Application No. 10-2014-0154536, filed on 11, 07, 2014, the entire contents of which are hereby incorporated by reference.

BACKGROUND OF THE INVENTION

The present invention relates to a composition including neural cells and an elastin-like polypeptide for treating Parkinson's diseases. More particularly, the present invention relates to a composition for treating Parkinson's diseases capable of more effectively increase a survival rate and settling rate of neural cells, which are transplanted to an acutely or chronically damaged nerve region to treat Parkinson's disease, by simultaneously administering neural cells with an elastin-like polypeptide.

Parkinson's disease is an incurable disease which causes motor disturbance, as dopamine-secreting neural cells get damaged. Although a therapeutic method using embryonic neural cell transplantation exists, it is difficult to secure a massive amount of cells, and there is a problem of a significantly low settling rate of transplanted cells and a survival rate of the settled cells. Thus, a method for increasing transplantation efficiency of transplanted cells has been actively studied.

For treatment of the Parkinson's disease, an optimal selection to optimize a microenvironment of living cells may become the case where cells are simultaneously transplanted with extracellular matrix (ECM) directly extracted from tissue of a damaged organ of an animal. However, there are drawbacks in which a specimen of derived ECM is complicate; there is limitation in high yield and mass production; and a cost is high. In addition, since in vivo derived ECM is most likely to cause an immune response, an unpredicted immune rejection response may occur in the case of in vivo transplantation. An immunosuppressant, which is used to suppress the immune rejection response, leads to concern about secondary infection. Therefore, a use of naturally occurring ECM with cells may be considered restrictive.

It has been known that TGPG[VGRGD(VGVPG)$_6$]$_{20}$WPC multiblock biopolymer (REP) (SEQ ID NO: 3) is effective in tissue regeneration, wherein the REP is prepared by repetitively fusing elastin valine-glycine-valine-alanine-proline-glycine (VGVPG) pentapeptide (SEQ ID NO: 1), which is one of elastin-like polypeptides (ELPs), and arginine-glycine-aspartate (ROD) ligand (Positions 3 to 5 of SEQ ID NO: 4) (Jeon et al., *J. Biomed. Mater Res. A.*, 97:152, 2011; Korean Registered Patent No. 1350900). One of advantages of REP is a response to changes in temperature, wherein the solubilized REP disrupts a coacervate into hydrophobic materials at a temperature equal to or above a particular transition temperature (Ts).

Korean Registered Patent No. 1350900, which is one of the typical techniques, discloses a biomimetic multiblock biopolymer for tissue regeneration and a tissue regenerating method using same.

As a result of constitutively trying to improve a therapeutic effect of neural cells on Parkinson's disease, the present inventors have complete the present invention by studying a potential of a matrix of an REP, and by identifying an effect of increasing a settling rate and survival rate of neural cells transplanted to an acutely or chronically damaged neural region when the REP and neural cells are administered together.

SUMMARY OF THE INVENTION

The present invention is derived to solve the above-mentioned problems. A first problem of the present invention to be solved is to provide a composition for treating Parkinson's disease, the composition including neural cells and an elastin-like artificial extracellular matrix (REP) prepared by repetitively fusing an elastin-like polypeptide and a ligand.

A second problem of the present invention to be solved is to provide a method for promoting treatment of Parkinson's disease including the neural cell and elastin-like polypeptide To solve the first problem of the present invention as describe above, the present invention includes a composition for treating Parkinson's disease including a neural cell; and an elastin-like artificial extracellular matrix (REP) prepared by repetitively fusing an elastin-like polypeptide and ligand.

According to a preferred embodiment of the present invention, the neural cell may be derived from mesencephalon derived neural stem cells or mesencephalon derived neural progenitor cells.

According to another preferred embodiment of the present invention, the elastin-like polypeptide may be elastin valine-glycine-valine-alanine-proline-glycine (VGVPG) polypeptide (SEQ ID NO: 1).

According to further another preferred embodiment of the present invention, the ligand may be arginine-glycine-aspartate (RGD) (Positions 3 to 5 of SEQ ID NO: 4) or arginine-glycine-aspartate-serine (RGDS) (SEQ ID NO: 2).

According to still another preferred embodiment of the present invention, the multiblock elastin-like artificial extracellular matrix may be [VGRGD(VGVPG)$_6$]$_n$ (n=10, 12, 15, 20) (SEQ ID NO: 4).

According to yet another preferred embodiment of the present invention, the composition for treating Parkinson's disease may include 25 to 100 μM of REP and $2\times10^4$ to $5\times10^4$ of neural cells.

The present invention includes a pharmaceutical composition for treating Parkinson's disease containing, as an active ingredient, the composition for treating Parkinson's disease as described above.

To solve a second problem of the present invention, the present invention includes a method for promoting treatment of Parkinson's disease using the composition for treating Parkinson's disease.

BRIEF DESCRIPTION OF THE DRAWINGS

FIG. 1A is the data obtained by measuring absorbance of the REP, FIG. 1B is a degree of aggregation of the REP in a coacervate state, FIG. 1C is a degree of inverse phase transition of Fam-REP, and FIG. 1D is a change in absorbance according to Fam-REP wavelength.

DETAILED DESCRIPTION OF PREFERRED EMBODIMENTS

Figure 1A:
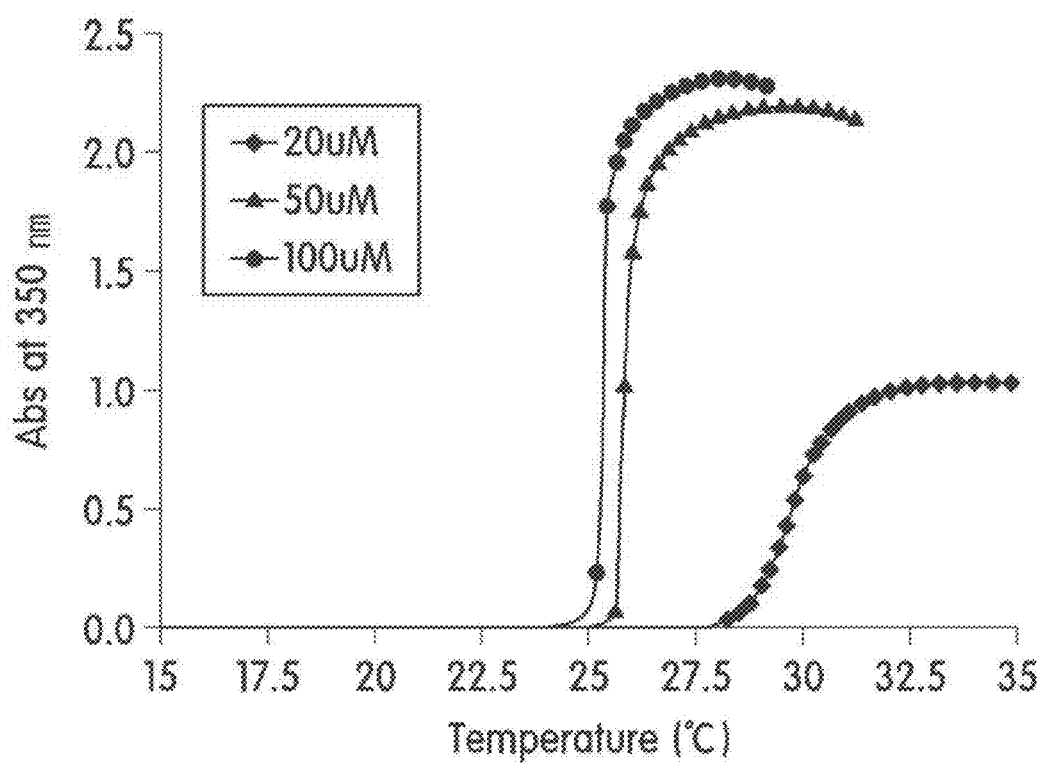
FIG. 1A, FIG. 1B, FIG. 1C and FIG. 1D are data investigating characteristic of an elastin-like artificial extracellular matrix (REP)

Hereinafter, the present invention will be described in more detail.

As described above, when neural cells are transplanted to an acutely or chronically damaged neural region, due to lack of oxygen or nutrients, in particular loss of cell-matrix interaction, considerable portions of transplanted cells become dead.

The present invention seeks to a resolution of problems described above by providing a composition for treating Parkinson's disease, wherein the composition includes neural cells; and an elastin-like artificial extracellular matrix (REP) prepared by repetitively fusing an elastin-like polypeptide and ligand. Through this, there is an effect of more effectively increasing a survival rate and settling rate of transplanted neural cells.

As used herein, the term "treatment" means an approach to obtain a beneficial or desirable clinical result. A clinical result, which is beneficial or desirable for the purpose of the present invention, includes alleviation of a symptom, reduction in a lesion, suppression of deterioration, delay in a progression rate of a disease, amelioration, or temporal alleviation and reduction of a disease state, but not limited thereto. In addition, "treatment" may mean prolong of a survival rate comparing to an expected survival rate when treatment is not performed. "Treatment" indicates both therapeutic treatment and preventive or prophylaxis measures. The treatment includes treatment required for previously developed disorders, as well as preventable disorders.

The present invention includes a composition for treating Parkinson's disease, the composition including neural cells; and an elastin-like artificial extracellular matrix (REP) prepared by repetitively fusing an elastin-like polypeptide and ligand.

As used herein, "neural cells" are major cells to form a nervous system, and capable of transferring a signal in an electrical method unlike other cells by expressing ion channels such as sodium channels and potassium channels. In addition, neural cells serve a role in receiving and storing various information by sending and receiving signals with adjacent neural cells through a structure termed synapse. In other words, "neural cells" are cells in a neuronal system, and interchangeably used with the term "neuron" or "neuronal cells".

As mention above, Parkinson's disease occurs as certain cerebral nerves secreting a neurotransmitter, i.e. dopamine, gradually become dead, and is treatable through a method, as one of therapy for the disease, in which an acutely or chronically damaged neural region is ameliorated into a biological environment suitable for regeneration. In other words, Parkinson's disease may be treated by administering, from outside, cells known to be essential for inducing regeneration, i.e. neural cells of the present invention, to an acutely or chronically damaged neural region.

"Neural cells" of the present invention may be dopaminergic neural cells. In other word, "neural cells", which express tyrosine hydroxylase (TH), are specifically located at mesencephalic substantia nigra, and modulate postural reflex, movement, and reciprocal behaviors by stimulating striatum, limbic system and neocortex in the body. In particular, mesencephalic characteristic is essentially required to substantially serve a role as in vivo dopaminergic neural cells.

In the present invention, the neural cells may be mesencephalon-derived neural stem cells or mesencephalon-derived neural progenitor cells, and the mesencephalon-derived neural stem cells or mesencephalon-derived neural progenitor cells may be differentiated into dopaminergic neural cells.

"Stem cells" generically refers to undifferentiated cells in the step before differentiation into each cell constituting tissue. Stem cells have a mitotic ability and also an ability to be differentiated into a particular cell when differentiating stimulation is applied so that the stem cells have plasticity which leads differentiation into final cells having different characteristic depending on an environment or stimulation. In addition, stem cells may be divided into embryonic stem cells and adult stem cells according to origin of development.

"Differentiation" refers to a phenomenon in which structures and functions of cells become specialized, as cells are divided, proliferated and grow, i.e. the change in morphology and functions allowing cells, and tissue of an organism to perform a job given to each of them. As a final step of the development process leading to specialization of cells, cell differentiation is a phenomenon in which activities of genes in cells become different from each other such that genes are expressed in a manner different from each other. Consequently, each cell has characteristic completely different from each other in terms of a structure and function.

"Neural progenitor cells" are undifferentiated progenitor cells, which have a multi-differentiation ability capable of being differentiated into neurogliocytes including neural cells, astrocyte cells and oligodendrocyte cells, and may be derived from brain tissue of a developing embryo or a brain of an adult.

In the present invention, the elastin-like polypeptide may be elastin valine-glycine-valine-alanine-proline-glycine (VGVPG) polypeptide (SEQ ID NO: 1), and the ligand may be arginine-glycine-aspartate (RGD) (Positions 3 to 5 of SEQ ID NO: 4) or arginine-glycine-aspartate-serine (RGDS) (SEQ ID NO: 2).

In other words, the elastin-like artificial extracellular matrix (hereinafter, designated as "REP") of the present invention is characterized by being prepared through repetitive fusion of VGVPG peptide (SEQ ID NO: 1) with RGD (Positions 3 to 5 of SEQ ID NO: 4) or RGDS (SEQ ID NO: 2), and preferably is $[VGRGD(VGVPG)_6]_n$ (n=10, 12, 15, 20) (SEQ ID NO: 4).

The VGRGD means valine-glycine-arginine-glycine-aspartate.

Figure 1B:
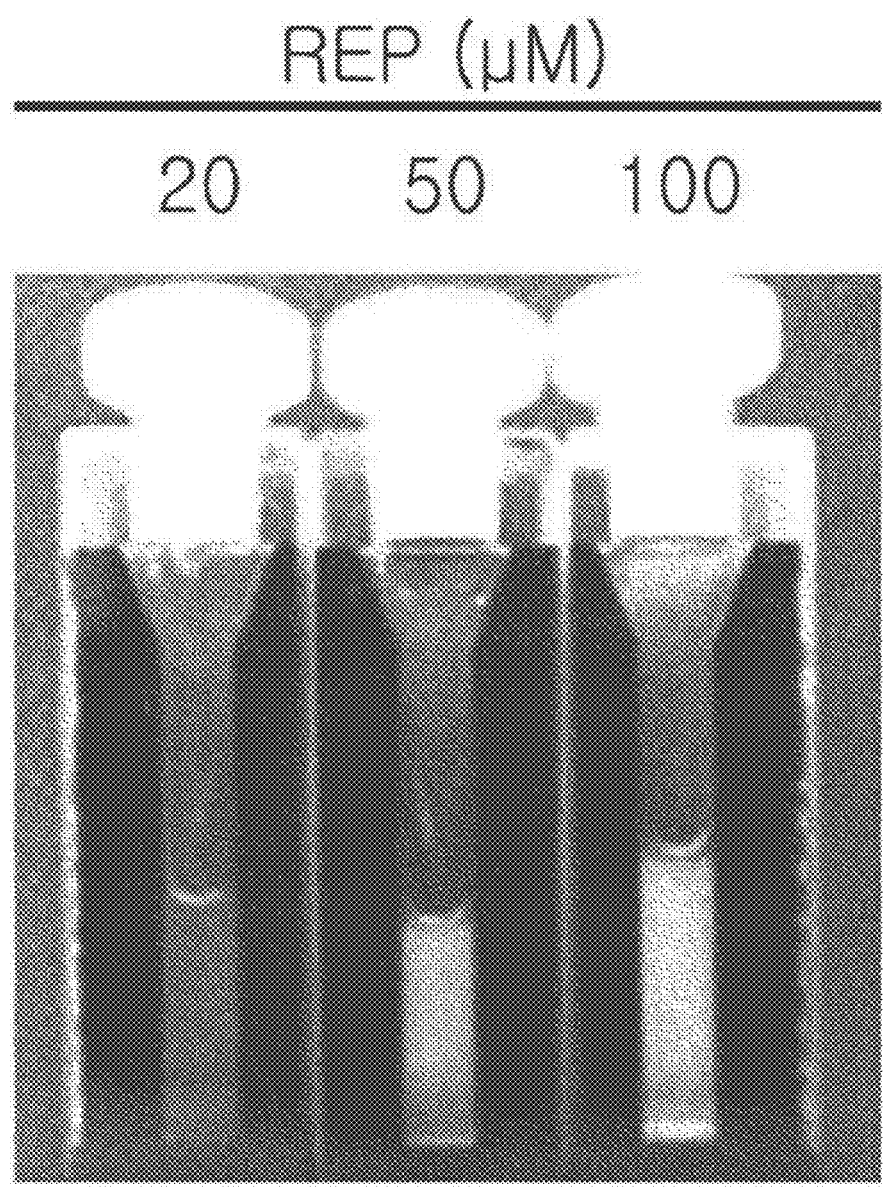
Figure 1C:
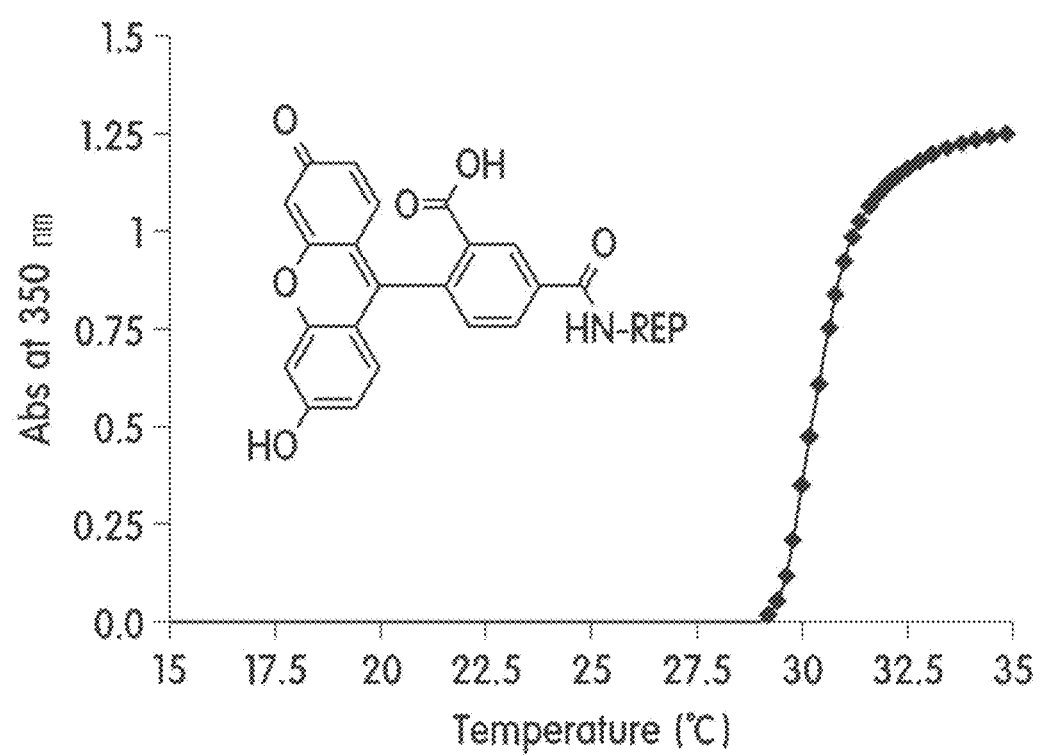
Figure 1D:
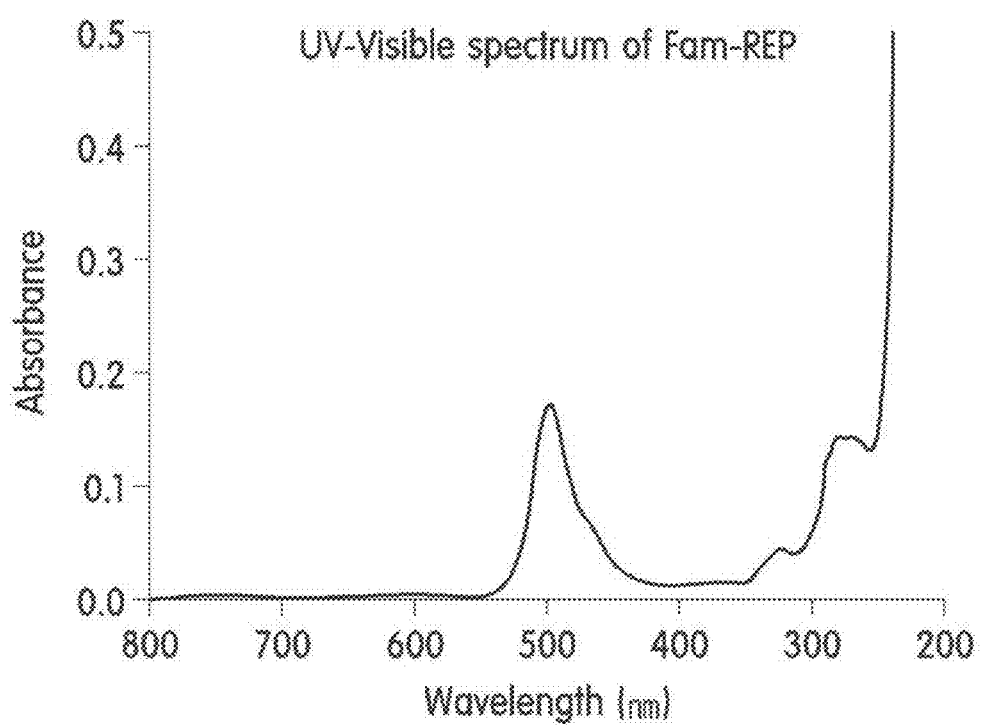

According to one example of the present invention, the REP is prepared by a known method (Jeon W B et al., *J. Biomed. Mater. Res. A*, 97:152, 2011), and the characteristic of REP was investigated by preparing REP labeled with Fam (Fam-REP). In the presence of DTT, as a result of measuring a degree of inverse phase transition of the REP, it has been observed that absorbance is rapidly increased at 25° C. or above (FIG. 1A), and degrees of aggregation of REP depending on concentrations are investigated in a coacervate state at 35° C. (FIG. 1B). Moreover, as shown in FIGS. 1C and 1D, it has been found that absorbance of the Fam-REP is increased at 30° C. or above, and a peak appears in the 500 nm range. That is to say, since particular transition temperatures ($T_t$) of REP and Fam-REP are lower than the body temperature of mice, the REP and Fam-REP may be aggregated into a coacervate state in an acutely or chronically damaged neural region.

In the present invention, the composition for treating Parkinson's disease may include 25 to 100 µM of REP and $2\times10^4$ to $5\times10^4$ neural cells, preferably 40 to 60 µM of REP and $3\times10^4$ to $4\times10^4$ of neural cells. The case where a lower concentration of REP and lower number of neural cells are included with respect to the above range may cause a problem in which a survival rate and settling rate of neural cells transplanted into an acutely or chronically damaged neural region are reduced. Further, it is possible to use a higher concentration of the REP and greater number of neural cells with respect to the above range, however it can be found that the above range is sufficient to achieve an effect in enhancement of a survival rate and settling rate of transplanted neural cells. In addition, in the case where concentration of REP becomes 100 µM or above, efficacy does not become outstanding in the concentration dependent manner, and an additional concentrating process is required to establish the concentration of 100 µM or above, which causes a problem in suitability in terms of costs. Also, when neural cells are administered in an amount greater than the above range, an effect of neural cells transplantation may not be greatly enhanced in a concentration dependent manner.

In an example of the present invention, to investigate efficacy of coadministration of neural cells and REP, mice used as an animal model for Parkinson's disease are respectively divided into a group only treated with neural progenitor cells (NPCs) (hereinafter, referred to as "NPC treated group"), which are one of neural cells of the present invention, and a group treated with a mixture of NPCs and REPs (hereinafter, referred to as "NPC-REP mixture treated group), and quantitative analysis on transplanted neural cells is carried out to investigate an effect of increasing a settling rate and survival rate of transplanted neural cells with lapse of time.

Figure 3:
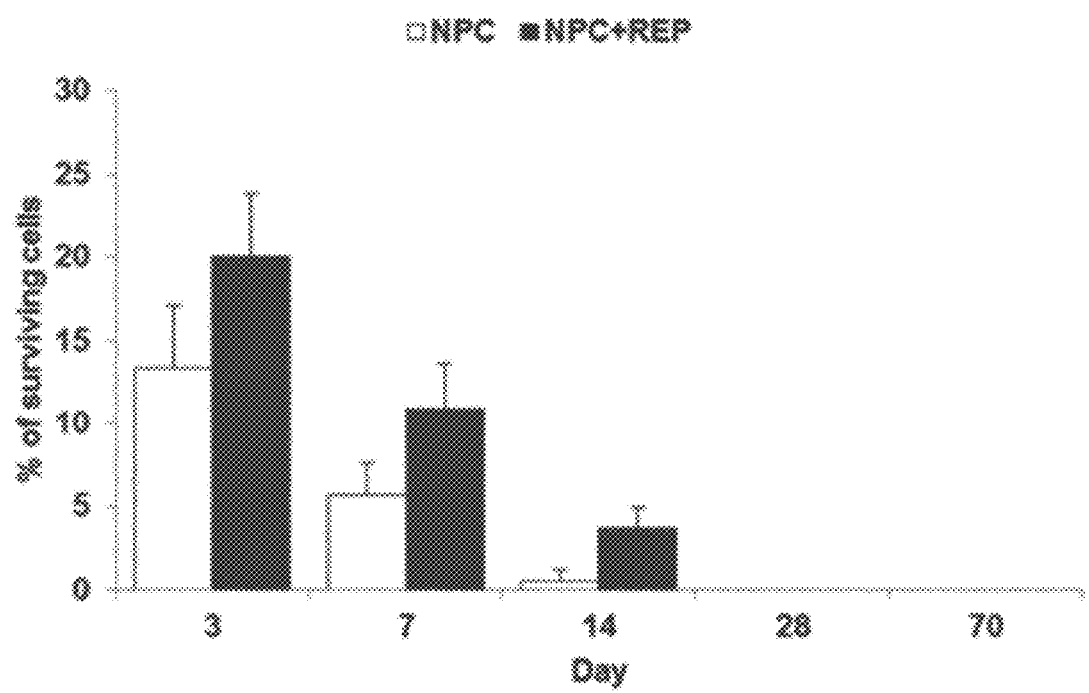
FIG. 3 is data obtained by investigating degrees of survival rates of transplanted cells for each group according to Example 2 of the present invention.

Firstly, FIG. 3 shows investigation of degrees of survival rates of neural cells transplanted to each group of mouse according to example 2 of the present invention.

As shown in FIG. 3, it has been found that the survival rates of neural cells of the NPC-REP mixture-treated group measured at 3, 7, and 14 days after transplantation are higher than the survival rates of neural cells of the NPC-treated group by at least 5%.

In other word, when neural cells are transplanted to an acutely or chronically damaged neural region, the survival rate of neural cells may be maximized in the case where the NPC-REP mixture is administered when compared to the case where the NPC are administered alone.

Figure 4:
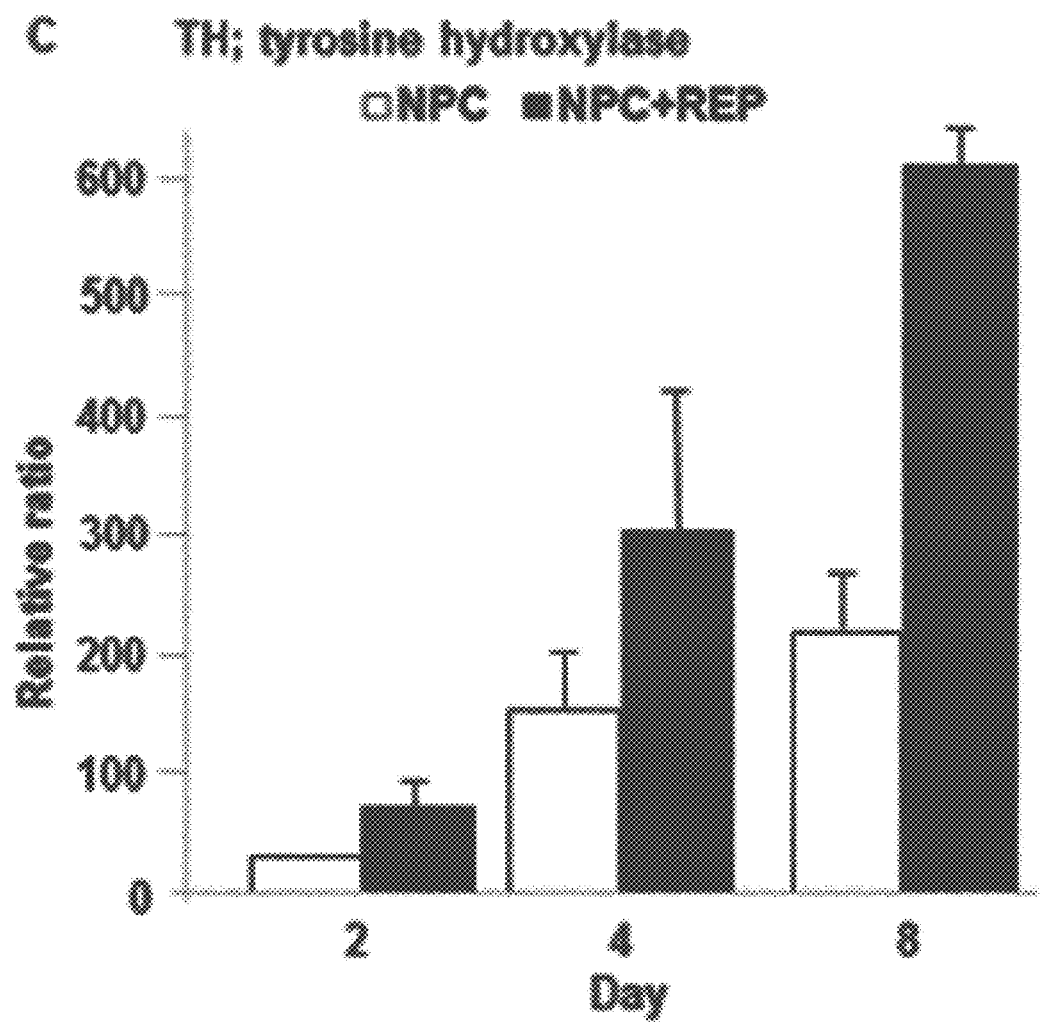
FIG. 4 is data obtained by measuring an effect of recovering a function of neural cells for each group according to Example 3 of the present invention.

FIG. 4 shows a result of measuring an effect of recovering a function of neural cells transplanted to each group of mouse according to Example 3 of the present invention.

As shown in FIG. 4, it has been found that expression rates of tyrosine hydroxylase of neural cells of the NPC-REP mixture-treated group measured at 2, 4, and 8 days after transplantation are higher than expression rates of tyrosine hydroxylase of neural cells of the NPC-treated group.

Additionally, an excellent effect on expression of dopaminergic neural cells can be demonstrated through a gradually increased expression rate of tyrosine hydroxylase of neural cells of the NPC-REP mixture-treated group measured at 2, 4 and 8 days after transplantation.

Further, the present invention includes a method for promoting treatment of Parkinson's disease using the composition for treating Parkinson's disease.

Furthermore, the present invention may include a pharmaceutical composition for treating Parkinson's disease containing the composition for treating Parkinson's disease as an active ingredient. In addition, the pharmaceutical composition for treating Parkinson's disease may be formulated by the method known in the pharmaceutical field, and formulated to a typical pharmaceutical preparation with various formulations such as liquid, ointment, emulsion, gel, cream, and paste by a structure itself or being mixed with a pharmaceutically acceptable carrier, and excipient. A dosage of the therapeutic agent of Parkinson's disease of the present invention is not specifically limited, and although the preferred dosage varies depending on conditions and weights of patients, severity of a disease or condition, type of a drug, and periods, the preferred dosage may be appropriately selected by a person skilled in the art. To achieve a preferred effect, the therapeutic agent of the present invention may typically be administered in a dose of 25 to 100 µM, and preferably 40 to 60 µM per injury on a day. Administration may be performed once or several times a day.

Hereinafter, the present invention will be described in more detail with reference to examples. These examples are provided to only illustrate the present invention, and it will be obvious to a person skilled in the art that the scope of the present invention is not construed being limited to these examples.

EXAMPLE

Example 1

1-1 Preparation and Characterization of Elastin-Like Artificial Extracellular Matrix (REP)

Purification of REP and identification of particular transition temperature (T) were performed by the method same as that described in the journal (Stimulation of fibroblasts and neuroblasts on a biomimetic extracellular matrix consisting of tandem repeats of the elastic VGVPG domain (SEQ ID NO: 1) and RGD motif (Positions 3 to 5 of SEQ ID NO: 4) (Jeon W B et al., J. Biomed. Mater. Res. A, 97:152, 2011)).

The REP was prepared as follows: to conjugate 5-carboxyfluorescein (Fam) at the N-terminal of the prepared REP, 5-carboxyfluorescein N-succinimidyl ester (sigma, USA) was dissolved in 580 µl DMSO such that the resultant has concentration of 5 µmol, and then 20 ml of PBS including 0.97 mol of the REP was added. The mixture was reacted for 3 hours at room temperature to prepare REP labeled with Fam (Fam-REP). The Fam-REP was purified by inverse phase transition. A degree of labeling was measured according to the protocol included in the AnaTag™ protein labeling kit (AnaSpec, USA).

In the presence of DTT, a degree of inverse phase transition of the REP was measured according to changes in temperature and REP concentrations (20, 50, and 100 µM). Temperature was increased at the rate of 1° C./min. Consequently, it can be observed that absorbance was rapidly increased at 25° C. or above (FIG. 1A), and REP aggregation in a coacervate state at 35° C. was measured depending on concentrations (FIG. 1B).

In addition, in the presence of DTT, as a result of measuring degrees of inverse phase transition of the Fam-REP, absorbance was increased at 30° C. or above (FIG. 1C), and, as a result of measuring changes in absorbance depending on Fam-REP wavelength by using UV-visible spectrum (FIG. 1D), it has been found that a peak appears at the 500 nm range.

1-2 Preparation of Human-Derived Neural Progenitor Cell (NPC)

NPC (PN003-F) was purchased from dv biologics Co., and allowed to be attached to a plate coated with matrigel and cultured in a specified medium having the composition adjusted to that presented by dv biologics Co., under the condition of 37° C., and 5% $CO_2$. When cells are reached confluence of 70% in the culture plate, accutase treatment was performed to conduct sub-culture. The NPCs used for transplantation are NPCs which were sub-cultured at most 8 times (P≤8).

1-3 Preparation of Animal Model of Parkinson's Disease 8 week-old male C57BL/6 mice (20-30 g), which are specific pathogen free (SPF) animals, were purchased from Central Lab. Animal Inc. (Seoul, Korea). The C57BL/6 mouse is an animal model frequently used to prepare Parkinson's disease model in the study about treatment of a disease, and the mouse may be applied to other experiments.

The mice were kept in an animal facility adjusted to have temperature of 22±3° C. and relative humidity of 50±10% and 12 hours of light-on period and 12 hours of light-off period. A breeding cage and breeding density were as follows: during whole experimental periods, a mouse was accommodated in a breeding cage made of polycarbonate one by one; mice were freely fed with a solid feed for experimental animal (PMI Nutritional International, Richmond, USA), which was sterilized with radiation irradiation (13.2 kGy), as a feed; and mice were allowed to freely take water, which was filtered tap water, by using a water bottle.

The mice were accommodated for one week, and then 1-methyl-4-phenyl-1,2,3,6-tetrahydropyridine (MPTP) dissolved in phosphate buffered saline (PBS) was intraperitoneally administered five times at the 2 hour interval in the concentration of 20 mg/kg body weight. Five days thereafter, mice were used to establish an animal model of Parkinson's disease.

All processes of animal care and surgery were admitted by the committee of animal care and use of Daegu Gyeongbuk Institute of Science & Technology (DGIST).

1-4 Administration of NPC and REP to Prepare Model Animal of Parkinson's Disease To investigate efficacy of coadministration of NPC and REP, mice were divided into the NPC-treated group (treated with $3.5 \times 10^4$ NPC) and NPC-REP mixture-treated group (treated with $3.5 \times 10^4$ NPC and 50 μM of REP), and quantitative analysis on neural cell transplantation was performed.

Figure 2:
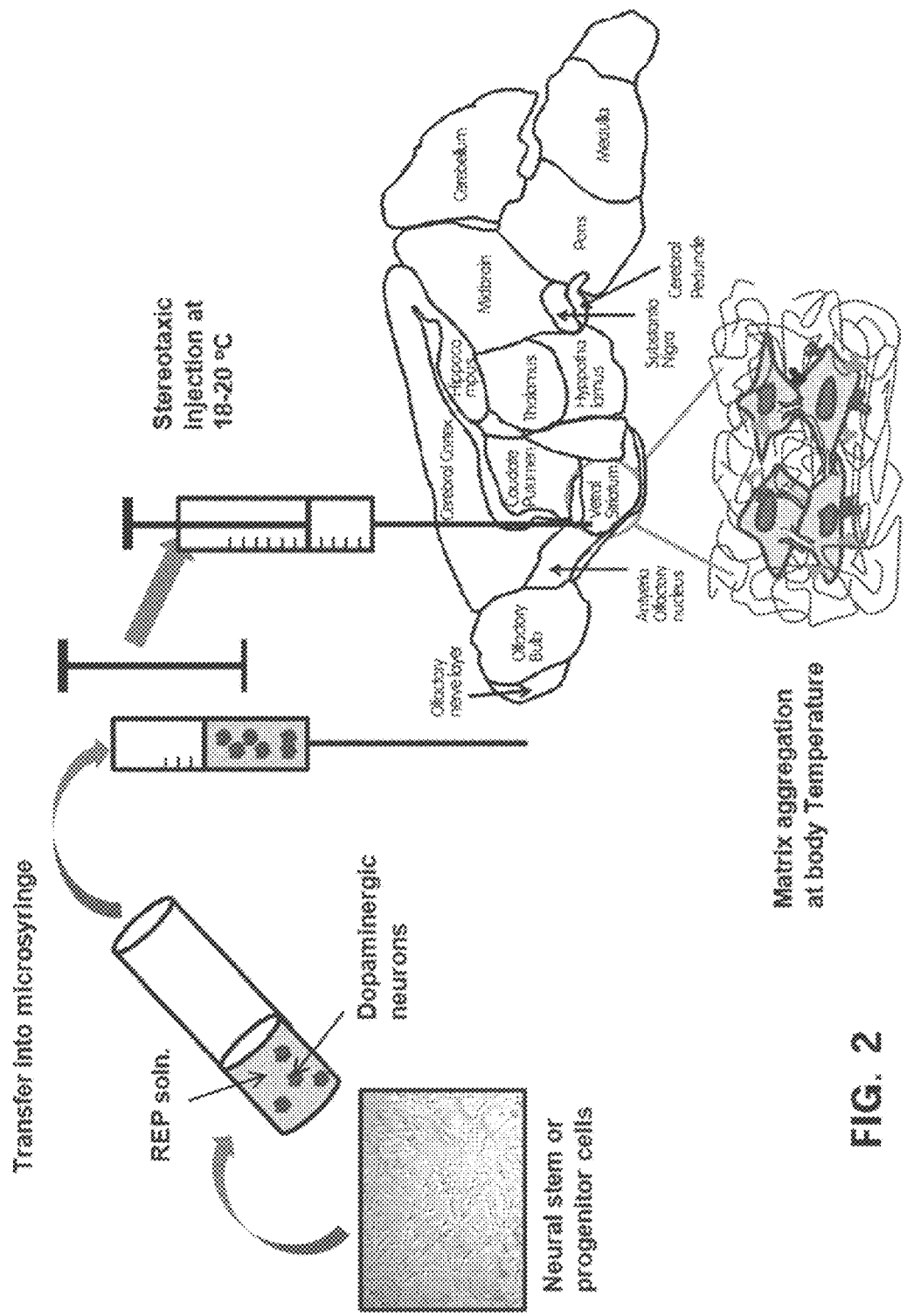
FIG. 2 is a schematic diagram showing a process of introducing neural cells for each group into Parkinson's disease model animals according to Example 1 of the present invention.

Specifically, to explain with referring to FIG. 2, each mouse was intraperitoneally injected with liquid of a mixture of 80 mg/kg of ketamine and 6 mg/kg of xylazine. An ear bar was firmly secured on a bone region of external auditory meatus in an anesthesia state in which behavior and response to pain does not occur. Then, a head region was secured on a stereotaxic frame from Narishige Co.

Thereafter, a right skull of each mouse was perforated with an electrical drill, and then, a Hamilton syringe was allowed to reach a position at 0.5 nm anterior, 2 nm lateral, and 3 nm ventral from bregma assumed as substantia nigra. Determination of the position was made by referring to the pictorial book of Paxinos and franklin. A solution for each group (2 μg/μl per each position) was injected through the Hamilton syringe over 3 minutes. One minute after injection, the syringe needle was drawn at the rate of 1 mm per minute. After injection of a drug, the hole in the skull was sealed with bone cement, and the incised skull was sutured. After about two hours of observation, when the mice reached a state where breathing was good and it is possible to sufficiently observe behaviors in the cage, mice were transferred to the mouse breeding room and bred under the condition same as that prior to treatment (FIG. 2).

Example 2

Measurement of Survival Rate of Transplanted Cells

A survival rate of NPCs, which were transplanted to brain tissue of each mouse in Examples 1-3, was analyzed through STEM121 or human nuclei-immunohistochemistry staining. After 3, 7, 14, 28, and 70 days of transplantation, each mouse was subjected to perfusion fixation (4% paraformaldehyde/50 mM phosphate buffered saline) via left ventricle. Then, the brain was extracted and fixed with 4% paraformaldehyde solution for 24 hours.

To prevent damage in tissue during freezing, tissue was allowed to stay in 30% sucrose at 4° C. for a day, and then the brain tissue was subjected to freezing microtome with cryostat (CM3000, Leica, Wetzlar, Germany) to become 30 um, and stored in a storing solution at 4° C.

STEM121 or human nuclei-immunohistochemistry staining was performed as follows: reaction with primary STEM121 or human nuclei antibody (rabbit anti-STEM121 or human nuclei antibody, 1:1000) followed by washing was performed; the resultant was cultured with a secondary antibody at room temperature for one hours, and then washed; the result was allowed for color-development by using ABC and DAB kit followed by dehydrogenation and clearer reaction with xylene; and then, the resultant was mounted with polymount and observed. For measuring an ability of a dense region of substantia nigra to be stained by STEM121 or human nuclei-immunohistochemistry staining, LSM 700 confocal microscope (Carl Zeiss) was used. The number of STEM121 or human nuclei-immunopositive cells was expressed as an average (%) obtained by counting the number of stained cells in a certain area of the tissue region of cells transplanted through stereooperation.

FIG. 3 shows investigation of survival rates of transplanted neural cells for each group of mouse according to Example 2 of the present invention. It has been found that survival rates of neural cells of the NPC-REP mixture-treated group measured at 3, 7, and 14 days after transplantation were higher than survival rates of neural cells of the NPC-treated group by at least 5%.

In other word, when neural cells are transplanted to an acutely or chronically damaged neural region, the survival rate of neural cells may be maximized for the case where the NPC-REP mixture are administered compared to the case where NPC are administered alone.

Example 3

Measurement of Effect of Recovering Function of Neural Cells

Tissue from the transplanted regions of each mouse, to which neural cells of the NPC-treated group and the NPC-REP mixture-treated group of Examples 1-3 were respectively transplanted, were isolated. In particular, an equivalent area of a striatum portion of each mouse was taken on 2, 4, and 8 days after transplantation to isolate RNA, and an expression rate of tyrosine hydroxylase, which is an indicator of dopaminergic neural cells, was investigated through qPCR (FIG. 4).

FIG. 4 is a result obtained by measuring an effect of recovering a function of neural cells transplanted to each group of mouse according to Example 3 of the present invention, and it has been found that expression rates of tyrosine hydroxylase of neural cells of the NPC-REP mixture-treated group measured at 2, 4, and 8 days after transplantation, were higher than expression rates of tyrosine hydroxylase of neural cells of the NPC-treated group.

Additionally, an excellent effect on expression of dopaminergic neural cells in the transplanted region can be demonstrated through gradually increased expression rates of tyrosine hydroxylase of neural cells of the NPC-REP mixture-treated group measured at 2, 4 and 8 days after transplantation.

The composition for treating Parkinson's disease including neural cells and an elastin-like polypeptide of the present invention has the effect of effectively increasing a settling rate and survival rate of neural cells transplanted to an acutely or chronically damaged neural region through interaction between REP and neural cells.

Hereinabove, the particular features of the present invention are described in detail, however, it will be apparent to a person skilled in the art that foregoing detailed description is to be construed as a preferred embodiment, and the scope of the present invention is not limited thereto. Therefore, the substantial scope of the present invention will be defined by accompanying claim and equivalents thereof.

What is claimed is:

1. A composition for increasing survival rate of a neural cell, the composition comprising:
 a neural cell; and an elastin-like artificial extracellular matrix (REP), wherein the neural cell is a mesencephalon-derived neural stem cell or a mesencephalon-derived neural progenitor cell,
 wherein the elastin-like artificial extracellular matrix is [VGRGD(VGVPG)$_6$]$_n$ (n=10, 12, 15, or 20) (SEQ ID NO: 4); and
 wherein the elastin-like artificial extracellular matrix has a concentration ranging from 40 to 60 μM and the number of the neural cells is $3 \times 10^4$ to $4 \times 10^4$.

2. A pharmaceutical composition for treating Parkinson's diseases containing, as an active ingredient, the composition for increasing survival rate of a neural cell of claim 1.

3. The composition for increasing survival rate of a neural cell of claim 1, wherein n=10, 12 or 15.

4. The pharmaceutical composition of claim 2, wherein n=10, 12 or 15.

* * * * *

```
SEQUENCE LISTING

<160> NUMBER OF SEQ ID NOS: 4

<210> SEQ ID NO 1
<211> LENGTH: 5
<212> TYPE: PRT
<213> ORGANISM: Artificial
<220> FEATURE:
<223> OTHER INFORMATION: Elastin-like polypeptide

<400> SEQUENCE: 1

Val Gly Val Pro Gly
1               5

<210> SEQ ID NO 2
<211> LENGTH: 4
<212> TYPE: PRT
<213> ORGANISM: Artificial
<220> FEATURE:
<223> OTHER INFORMATION: Ligand

<400> SEQUENCE: 2

Arg Gly Asp Ser
1

<210> SEQ ID NO 3
<211> LENGTH: 17
<212> TYPE: PRT
<213> ORGANISM: Artificial
<220> FEATURE:
<223> OTHER INFORMATION: Multiblock biopolymer(REP)
<220> FEATURE:
<221> NAME/KEY: REPEAT
<222> LOCATION: (5)..(14)
<223> OTHER INFORMATION: 10, 12, 15 or 20 sequence repetitions
<220> FEATURE:
<221> NAME/KEY: REPEAT
<222> LOCATION: (10)..(14)
<223> OTHER INFORMATION: 6 sequence repetitions

<400> SEQUENCE: 3

Thr Gly Pro Gly Val Gly Arg Gly Asp Val Gly Val Pro Gly Trp Pro
1               5                   10                  15

Cys

<210> SEQ ID NO 4
<211> LENGTH: 10
<212> TYPE: PRT
<213> ORGANISM: Artificial
<220> FEATURE:
<223> OTHER INFORMATION: Elastin-like artificial extracellular
      matrix(REP)
<220> FEATURE:
<221> NAME/KEY: REPEAT
<222> LOCATION: (1)..(10)
<223> OTHER INFORMATION: 10, 12, 15 or 20 sequence repetitions
```

```
-continued

<220> FEATURE:
<221> NAME/KEY: REPEAT
<222> LOCATION: (6)..(10)
<223> OTHER INFORMATION: 6 sequence repetitions

<400> SEQUENCE: 4

Val Gly Arg Gly Asp Val Gly Val Pro Gly
1               5                   10
```